(12) United States Patent
Simmons et al.

(10) Patent No.: US 7,968,599 B2
(45) Date of Patent: Jun. 28, 2011

(54) FAST RELEASE SOLID FORMULATION, PREPARATION AND USE THEREOF

(75) Inventors: Robert D. Simmons, Martinsville, NJ (US); Serena Tongiani, Cranford, NJ (US); Keith Alan Freehauf, Stockton, NJ (US)

(73) Assignee: Intervet International B.V., Boxmeer (NL)

( * ) Notice: Subject to any disclaimer, the term of this patent is extended or adjusted under 35 U.S.C. 154(b) by 169 days.

(21) Appl. No.: 12/265,297

(22) Filed: Nov. 5, 2008

(65) Prior Publication Data

US 2009/0156683 A1  Jun. 18, 2009

Related U.S. Application Data

(60) Provisional application No. 60/986,902, filed on Nov. 9, 2007.

(51) Int. Cl.
*A61K 31/24* (2006.01)
(52) U.S. Cl. ........................ 514/534
(58) Field of Classification Search ............ 514/534
See application file for complete search history.

(56) References Cited

U.S. PATENT DOCUMENTS

| 4,311,857 A | 1/1982 | Nagabhushan |
| 4,582,918 A | 4/1986 | Nagabhushan et al. |
| 4,743,700 A | 5/1988 | Jommi et al. |
| 4,876,352 A | 10/1989 | Schumacher et al. |
| 4,973,750 A | 11/1990 | Nagabhushan et al. |
| 5,105,009 A | 4/1992 | Jommi et al. |
| 5,227,494 A | 7/1993 | Schumacher et al. |
| 5,352,832 A | 10/1994 | Wu et al. |
| 5,382,673 A | 1/1995 | Clark et al. |
| 5,567,844 A | 10/1996 | Jommi et al. |
| 5,663,361 A | 9/1997 | Towson et al. |
| 7,122,198 B1 | 10/2006 | Singh et al. |
| 2008/0145317 A1* | 6/2008 | Tongiani et al. ............ 424/43 |

FOREIGN PATENT DOCUMENTS

CN      1947699      4/2007

OTHER PUBLICATIONS

Moore, "Florfenicol", Journal of Exotic Pet Medicine, vol. 16, No. 1, pp. 52-54 (2007).
Material Safety Data Sheet, Florfenicol Powders, Schering Canada Inc., pp. 1-7 (Feb. 6, 2004).
International Search Report in corresponding PCT/US2008/082427, mailed Feb. 12, 2009.

* cited by examiner

*Primary Examiner* — Raymond J Henley, III

(57) ABSTRACT

The present invention relates to a chemically stable formulation of florfenicol, (and structurally related compounds) in compositions such as soluble blended powders, granules, fast-dissolving tablets or pellets suitable for rapid release of the drug in water, and to methods and kits for treating animals with aqueous compositions including florfenicol.

28 Claims, 3 Drawing Sheets

FAST RELEASE SOLID FORMULATION, PREPARATION AND USE THEREOF

RELATED APPLICATIONS

This application claims priority to provisional application U.S. Ser. No. 60/986,902, filed on Nov. 9, 2007.

BACKGROUND OF THE INVENTION

1. Field of the Invention

This invention includes methods and kits for treating animals with soluble solid dosage forms including florfenicol and pharmaceutically acceptable salts thereof, to be added to drinking water systems.

2. Description of the Related Art

Florfenicol is a broad spectrum antibiotic developed for use in veterinary treatments. Florfenicol is currently indicated for the control of mortality due to *E. coli* airsacculitis in broiler chickens, as well as for treatment and control of swine respiratory diseases associated with *Actinobacillus pleuropneumoniae*, *P. multocida*, *Mycoplasma*, *Salmonella cholera suis* and *Streptococcus suis* Type II.

The delivery of florfenicol as a soluble powder in the drinking water system is not an easy task. One of the challenges is its relatively low water-solubility (1.23 mg/mL). Another challenge associated with developing a soluble powder containing florfenicol is the drug's limited wettability in water. Upon addition to water, florfenicol floats on the surface and does not disperse evenly throughout the volume of water. Over the years, various techniques have been suggested to overcome these issues. Various pro-drug formulations and other solubilization techniques, such as the use of encapsulation and surfactants, have been proposed (see, e.g., U.S. Pat. No. 7,122,198). There are, however, some drawbacks associated with the prior formulations. For example, an organic concentrate solution creates disposal and storage issues. Furthermore, this type of product typically has a limited expiration date. Additionally, such formulations are not as palatable for the animal. Thus, it is desirable to seek additional compositions and methods to administer florfenicol in order to satisfy the needs of the industry.

SUMMARY OF THE INVENTION

In accordance with one aspect of the invention, there is provided a method for treating animals with florfenicol including the steps of:

a) providing a soluble solid dosage form-based florfenicol composition comprising:
   i) from about 20 to about 60 wt % of florfenicol or a pharmaceutically acceptable salt thereof,
   ii) from about 0.5 to about 5.0 wt % of a water soluble binding agent, and
   iii) from about 40 to about 80 wt % of a filler;

b) dissolving the composition of step a) in water; and c) administering the water containing the florfenicol to animals in need thereof.

In other aspects of the invention, the composition of step a) above consists essentially of elements i) through iii).

Another aspect of the invention includes kits which are useful in carrying the methods of treatment. The kits can include the aforementioned soluble solid dosage form-based florfenicol, instructions for dissolving or mixing the soluble solid dosage form-based florfenicol in water, and optionally instructions for treating animals with florfenicol-containing drinking water.

The development of a soluble solid dosage form-based composition that can be added directly to the drinking water with a fast solubility rate profile will introduce several advantages for the users in the field.

DETAILED DESCRIPTION OF THE INVENTION

Figure 1:
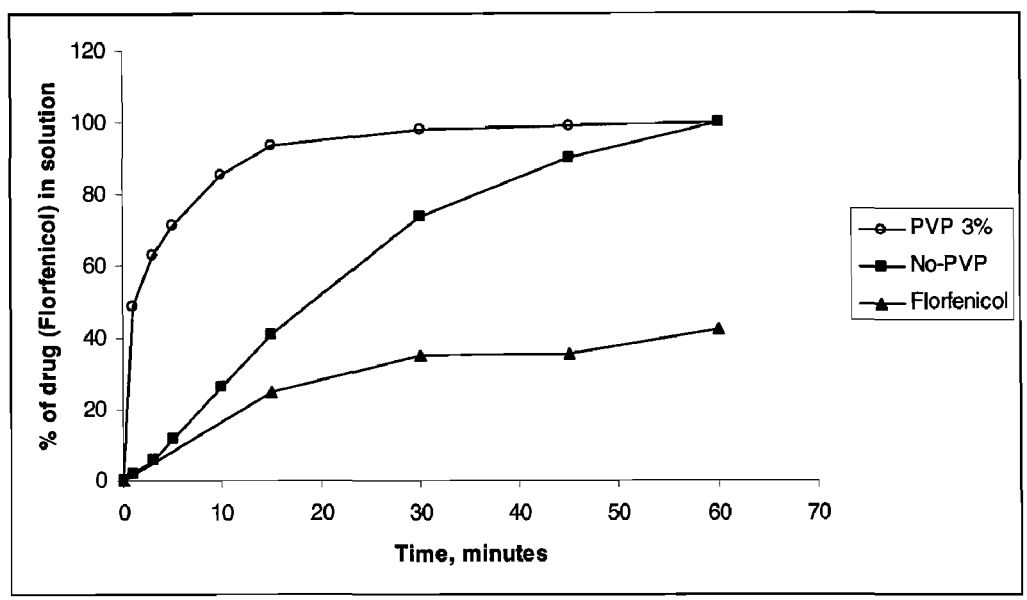
FIG. 1 illustrates the solubility rate profiles for samples prepared in Example 1.

The invention provides soluble solid dosage form antibiotic compositions for use in animal drinking water systems. In some preferred aspects of the invention, the compositions are in the form of granules, blended powders, fast dissolving tablets or pellets containing an effective amount of a water soluble binding agent which permits the composition to fully dissolve more rapidly, when compared to similar compositions under similar conditions without a water soluble binding agent. The granules are usually lower than 30 mesh, and the rapid dissolution can be achieved under little or no agitation. The composition of the present invention also contains a filler.

It is contemplated that animals can be treated with the compositions and by the methods of the present invention. For purposes of the present invention, "animal" shall be understood to include non-aquatic animals, including, but not limited to, swine, poultry and/or bovids (including calves and neo-natal calves). For purposes of the present invention, "bovid" shall be understood to include cattle and other members of this family (i.e., goats). For purposes of the present invention "soluble solid dosage form" shall be understood to include soluble powders, soluble granules, fast dissolving tablets or pellets suitable for rapid release of the drug in water.

The presence of a specific percentage of a water soluble binding agent such as polyvinylpyrrolidone K30 in the composition was found to enhance the wettability of the drug florfenicol, thereby providing a fast rate of solubility of the drug in water, and quickly facilitating the achievement of the target concentration. The florfenicol containing products currently on the market in the form of a powder are only approved and recommended for incorporation in to animal feed as premix for melt extrusion feed production or for top dressing of feed pellets, and are not recommend for direct addition into the animal drinking water.

One of the key components of the compositions of the invention is the drug florfenicol. Florfenicol can be prepared as a free base or in its salt form and also in any of its derivative forms, such as phosphate derivatives and any florfenicol pro-drugs. Florfenicol is not hygroscopic, so its incorporation in a composition does not cause instability due to water absorption. Florfenicol is also known as [R-(R*,S*)]-2,2-Dichloro-N-[1-(fluoromethyl)-2-hydroxy-2-[4-(methylsulfonyl)phenyl]-ethyl]acetamide. Processes for the manufacture of this preferred antibiotic, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361. Another preferred antibiotic is thiamphenicol. Pharmaceutically-acceptable salts of the foregoing are also contemplated for addition to the compositions described herein.

In some aspects of the invention, the amount of florfenicol included in the composition that is used for treating animals may range from about 20 to about 60 wt % of the composition. In some preferred aspects, the amount of florfenicol is from about 25 to about 50 wt % of the composition, while in more preferred aspects, the amount is from about 45 to about 50 wt %.

The compositions can contain a second pharmaceutically active compound that does not interfere or otherwise hamper the effectiveness of florfenicol. Such active compounds may include, for example, anti-inflammatory agents such as corticosteroids, NSAIDS, such as flunixin, COX-inhibitors and other analgesics, antiparasitic compounds such as, for example, an avermectin compound such as ivermectin, doramectin, milbemycin, selamectin, emamectin, eprinomectin, and moxidectin, and/or optionally a flukicide. It may also be preferred to employ a second antibiotic in the formulation. Preferred antibiotics may include tetracyclines. Particularly preferred is chlorotetracycline and oxytetracycline. Other preferred additional antibiotics include beta-lactams, such as penicillins, cephalosporins, e.g., penicillin, amoxicillin, or a combination of amoxicillin with clavulanic acid or other beta lactamase inhibitors, ceftiofur, cefquinome, etc. Also, preferred antibiotics include fluoroquinolones, such as, for example, enrofloxacin, danofloxacin, difloxacin, orbifloxacin and marbofloxacin, and macrolide antibiotics such as tilmicosin, tulathromycin, erythromycin, azithromycin and pharmaceutically-acceptable salts thereof and the like. Alternatively, one could include insect growth regulators in combination with the active compounds of the present invention.

In many preferred aspects of the invention, the compositions that are used for treating animals preferably contain a water soluble binding agent that enhances the wettability of the drug, and consequently the dissolution rate of the drug in water, and reduces the need to use organic solvents and expensive complexing agents in the composition which can affect the palatability and the stability of the composition. Acting as both a binding agent and a solubility rate enhancer, the water soluble binding agent in the compositions of the present invention also helps allow the manufacturing process to be more efficient when compared to prior art methods, because less heat and extrusion are necessary to obtain a fast solubility rate profile product. The water soluble binding agent also helps the active agent dissolve in water, and in some aspects of the invention, facilitates from about 80 to about 95% or more of the active agent being dissolved within the first 15 minutes. Consequently, the time that is necessary before the composition can be administered to a subject in need thereof is dramatically decreased. It has also been determined that therapeutic concentrations of the drug can be maintained in water for more than 72 hours. This property of the inventive compositions therefore substantially decreases the frequency of replacement of the medicated water for treatment.

A non-limiting list of water soluble binding agents includes polyvinylpyrrolidone, polyvinylpyrrolidone K30, sucrose, carboxy polymethylene (Carbopol), hydroxypropyl cellulose, starch, methylcellulose, sodium carboxymethylcellulose, polyacrilamide, polyvinyl alcohols, mixtures thereof, and the like. The water soluble binding agent is preferably polyvinylpyrrolidone having a K value (viscosity in aqueous solution relative to that of water) of 25 to 35.

The amount of the water soluble binding agent included in the inventive compositions can range from about 0.5 to about 5 wt %. Preferably, the amount is from about 2.5 to about 3.5 wt % of the composition, and more preferably from about 2.5 to about 3.0 wt % of the composition. In one particular embodiment, the water soluble binding agent is polyvinylpyrrolidone present in an amount of from about 2.5 to about 3.5 wt % of the composition. In another particular embodiment, the polyvinylpyrrolidone is present in an amount of from about 2.5 to about 3 wt % of the composition.

The compositions of the invention also preferably include a filler or a mixture of fillers. The fillers increase the bulk volume so that the final product has the proper volume for user handling. Non-limiting examples of fillers include lactose, sucrose, mannitol, sorbitol, calcium carbonate, mixtures thereof, and the like. In some particular embodiments, the filler is lactose.

The amount of the filler present in the composition that is used for treating animals can be from about 40 to about 80 wt % of the composition. In some particular embodiments, the filler is present in amounts of from about 50 to about 75 wt % of the composition. Other particular embodiments include the filler in amounts of from about 65 to about 70 wt % of the composition. In one particular embodiment, the filler is lactose present in an amount of from about 50 to about 75 wt % of the composition. In another particular embodiment the lactose is present in an amount of from about 65 to about 75 wt % of the composition.

Conventional excipients, such as colorants, fillers, diluents, surfactants, wetting agents, sweeteners, flavorings, preservatives, antioxidants, stabilizers, as well as other ancillary pharmaceutically acceptable ingredients and the like, and mixtures thereof, may be added to the formulations. For example, the formulations can also contain additional common excipients such as binders, lubricants, diluents, surfactants, solvents and mixtures thereof. One particular diluent is lactose anhydrous. Other diluents that are suitable include, without limitation, microcrystalline cellulose, sorbitol, starch and calcium phosphate. The amount of diluent can range from about 0 to about 40 wt %. One particular lubricant is magnesium stearate, but other suitable lubricants can include, without limitation, calcium phosphate and/or calcium phosphate di-basic. The amount of the lubricant can range from about 0 to about 5 wt %. One particular surfactant is Tween80, but other suitable surfactants can include, without limitation, sodium lauryl sulfate or mixtures thereof. The amount of the surfactant can range from about 0 to about 10 wt % of the composition, particularly from about 1 to about 10 wt % of the composition, particularly, from about 1 to about 5% of the composition, and more particularly from about 1 to about 3.5 wt %.

In some particular embodiments, the wetting agent can be povidone, carbopol, sodium dodecyl sulfate, sodium lauryl sulfate, a mixture thereof, and the like. The amount of the wetting agent can range from about 0 to about 10 wt % of the composition, particularly from about 1 to about 10 wt % of the composition, particularly, from about 1 to about 5% of the composition, and more particularly from about 1 to about 3.5 wt %.

Other optional inert ingredients may be added to the composition, as desired. Such ingredients can include preservatives, antioxidants, stabilizers, colorants, sweeteners and flavorings. Exemplary preservatives include methyl p-hydroxybenzoate (methylparaben) and propyl p-hydroxybenzoate (propylparaben). Exemplary antioxidants include butylated hydroxyanisole and sodium monothioglycerol. Exemplary stabilizers for use in the present invention include, for example, BHT or citric acid. One particular stabilizer to prevent degradation of any of the active ingredients in the formulations of the present invention is BHT, present in a concentration between 0.01% (w/w) and 0.05% (w/w). Other suitable stabilizers include, for example, fumaric acid, malic acid, and tartaric acid. Exemplary sweeteners include mannitol, lactose, sucrose and dextrose.

In other aspects of the invention, there are provided methods of treating or preventing florfenicol-susceptible conditions. These methods include dissolving a sufficient amount of the composition described herein into water, and administering the resultant solution to a subject in need thereof, as part of a liquid to be ingested by the subject, e.g., the formulation may be added into the subjects drinking water system to administer the treatment and therapeutic dose.

The amount administered to a subject in need thereof is a therapeutically or prophylactically-effective amount of the florfenicol solution resulting from the introduction of the compound into water. In most aspects of this embodiment, the amount of the compound added to water is an amount that is sufficient to bring the concentration of florfenicol in the drinking water to from about 0.01 mg/mL to about 0.2 mg/mL. Preferably, the concentration will be about 0.1±0.09 mg/mL in the bulk drinking water, and a concentration of about 13.5±0.1 mg/mL when the aqueous solutions are used in a typical proportioner mixing ratio of 1:128 gallons. Depending upon the condition being treated and the type, size, weight, etc. of the animal being treated, it is contemplated that suitable periods of treatment will range from about 1 to about 5 days, or longer if needed, using the compounds in drinking water at the concentrations mentioned above. As will be appreciated by those of ordinary skill, the animals will drink the treated water ad libitum. It is nonetheless contemplated that sufficient amounts of the florfenicol will be administered to the animals in need thereof when it is available for drinking for the periods mentioned above.

The compositions of the present invention may, if desired, be presented in a pack or dispenser device, such as an FDA approved kit, which may contain one or more unit dosage forms containing the compound in the form of a stable powder, granules, fast-dissolving tablets or pellets containing the active ingredient. The pack may, for example, comprise metal or plastic foil, such as a blister pack. The pack may also consist of a soluble biodegradable pouch ready to use, sealed in a metal plastic foil. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be the labeling approved by the U.S. Food and Drug Administration for prescription drugs or of an approved product insert. Compositions including a compound of the invention formulated in a compatible pharmaceutical carrier may also be prepared, placed in an appropriate container, and labeled for treatment of an indicated condition. Thus, the kit can be used in connection with treating or preventing a bacterial infection or other disease in a subject in need thereof, and include a sufficient amount of the composition described herein and instructions for introducing the composition into drinking water to be given to the subject in need thereof. In one particular embodiment, the kit is used for treating an animal with a soluble solid dosage form based florfenicol composition comprising from about 20 to about 60 wt % of florfenicol or a pharmaceutically acceptable salt thereof, from about 0.5 to about 5.0 wt % of a water soluble binding agent, and from about 40 to about 80 wt % of a filler, instructions for dissolving the soluble solid dosage form-based florfenicol composition in water, and optionally instructions for treating the animal with the water containing the florfenicol.

An exemplary method of preparing the granules of the present invention can be achieved by dry blending florfenicol and a preferred additive such as lactose, and thereafter achieving wet granulation with a PVP30 solution in purified water. The granules are then dried in an oven at approximately 50° C. for approximately 3 hours. Next, the granules are milled and screened using a stainless screen until the particles are below 30 mesh.

An exemplary method of preparing a blended powder of the present invention can be achieved by screening the florfenicol and a preferred diluent through a stainless screen until the particles are below 30 mesh, and consequently dry blending the two components.

It will be understood by those of ordinary skill that other delivery systems, such as compressed tablets, pellets, etc., can be made using techniques well known in the art without undue experimentation.

The development of a soluble solid dosage form-based product that can be added directly to the drinking water with a fast solubility rate profile will introduce several advantages for the users in the field. For example, a soluble solid dosage form formulation would overcome disposal/storage problems associated with the high volume of organic solvents, and would practically eliminate stability issues that can occur with liquid products and will improve the palatability issues associated with high levels of organic solvents. Moreover, such formulations for direct addition in the drinking water represent a significant advantage because they facilitate the administration of the product to multiple animals.

EXAMPLES

The following Examples are provided to illustrate certain embodiments of this invention and are not intended, nor are they to be construed, to limit its scope in any manner whatsoever.

To determine the solubility profile of different formulations, dissolution was performed using USP apparatus 2 with paddle agitation at 50 rpm. The dissolution medium was Milli-Q water maintained at a temperature of 25° C. The formulations were added directly to the water in the correct amount to achieve a final concentration of 0.1 mg/mL of florfenicol. Aliquots of the resulting solution were withdrawn and analyzed using either UV-VIS spectrophotometry or HPLC, the latter to exclude excipient contribution or degradation of florfenicol. For HPLC analysis, an organic/aqueous mobile phase was used for the separation on a C18, reverse phase column. Detection was performed by UV absorption spectrometry. The percent dissolved was calculated versus an external reference standard prepared at the nominal concentration of the analyte.

Example 1

Pure florfenicol was analyzed as a comparator to assess the effectiveness of the formulation. As illustrated in FIG. 1, pure florfenicol was only approximately 25% dissolved within 15 minutes and approximately 43% dissolved within 60 minutes.

As an inventive example, florfenicol formulated as soluble granules using 3 wt % PVP30 and 47 wt % lactose was prepared. Florfenicol and lactose were blended dry, and a wet granulation was achieved with a PVP30 solution in purified water. The granules were dried in an oven at 50° C. for 3 hours. The granules were triturated and screened using a stainless screen until the granules were below 30 mesh. FIG. 1 demonstrates that the florfenicol of this inventive composition was at least 80% dissolved within 15 minutes and approximately 100% dissolved within 30 minutes.

Also for comparative purposes, florfenicol was dry blended with lactose without the use of PVP. As shown in FIG. 1, the florfenicol of this comparative composition was approximately 35% solubilized in the first 15 minutes, and approximately 100% solubilized within 60 minutes.

In accordance with the present invention, the composition of the formulation of the present invention including a water soluble binding agent increased the florfenicol rate of dissolution, and allowed a practically complete dissolution within 15 minutes after addition to water.

Example 2

Figure 2:
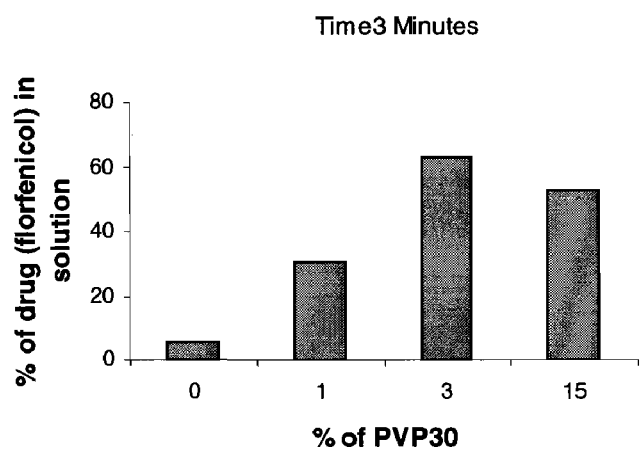
FIG. 2 illustrates florfenicol solubility in water after 3 minutes in formulations containing different percentages of PVP30.
Figure 3:
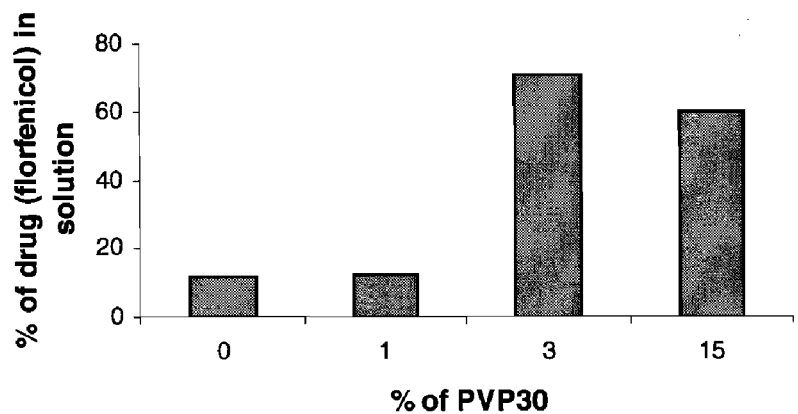
FIG. 3 illustrates florfenicol solubility in water after 5 minutes in formulations containing different percentages of PVP30.
Figure 4:
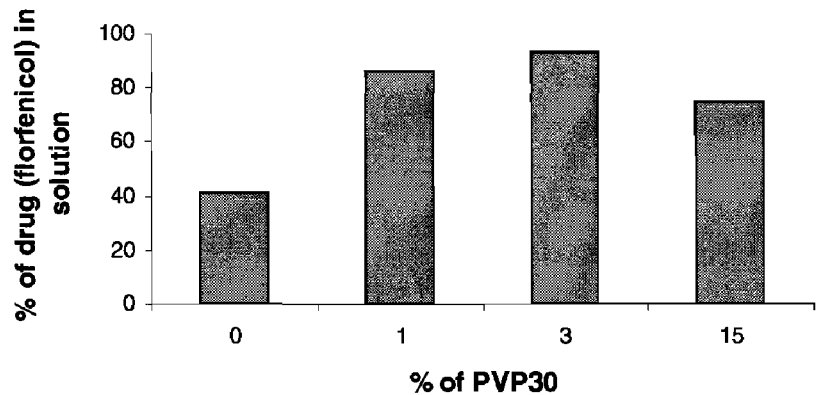
FIG. 4 illustrates florfenicol solubility in water after 15 minutes in formulations containing different percentages of PVP30.

PVP30 was analyzed to determine its role in acting as a solubility enhancing agent for the active ingredient florfenicol. The solubility rate profiles for florfenicol were determined in the presence of varying percentages of PVP30. In FIGS. 2, 3 and 4, the solubility of the drug florfenicol is reported against varying percentages of PVP30 in different formulations at different times. All the formulations described in these Figures were prepared as soluble granules in the same manner described in Example 1.

As illustrated in FIGS. 2, 3 and 4, the percent of florfenicol in solution after 3, 5 and 15 minutes was the greatest when PVP30 was present in an amount of approximately 3.0 wt % of the composition. Further observation indicated that the percent of florfenicol in solution after 3, 5 and 15 minutes was the greatest when PVP30 was present in an amount from about 2.0 to about 3.5 wt % of the composition.

Example 3

The role of PVP as a preferred solubility rate profile enhancer was demonstrated by comparing PVP with different water soluble binding agents.

Figure 5:
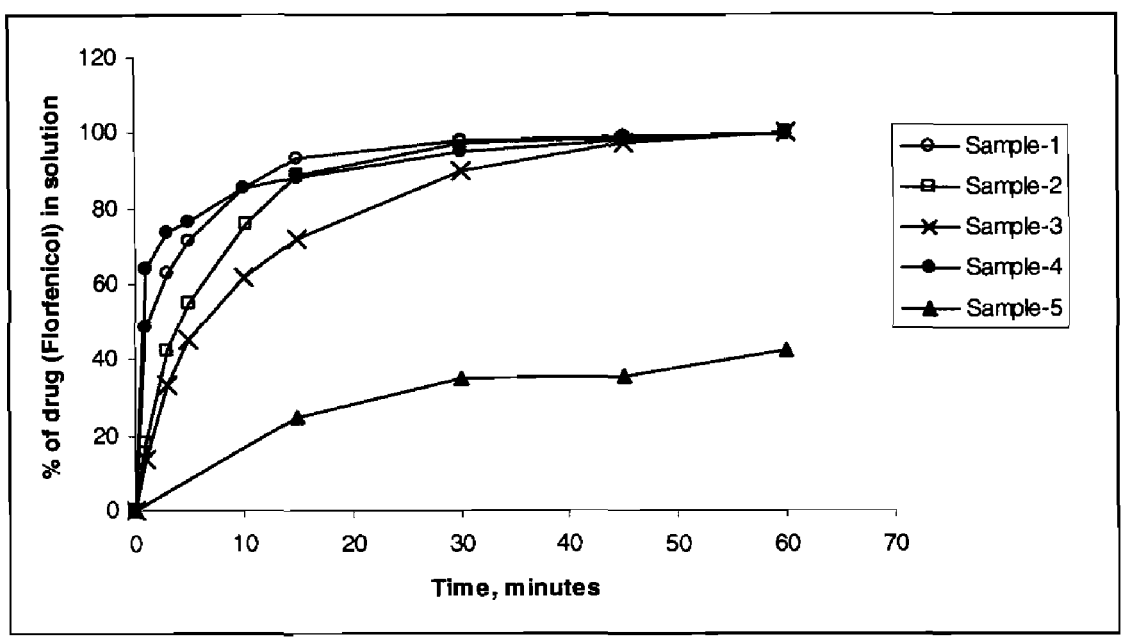
FIG. 5 illustrates the solubility rate profiles for florfenicol formulated in granules using different water soluble binding agents.

As shown in FIG. 5, Sample 1 shows the solubility rate profile for granules formulated with a binder solution containing 50% w/w florfenicol, 47% w/w lactose and 3% w/w PVP30. Sample 2 shows the solubility rate profile for granules formulated with a binder solution containing 50 wt % florfenicol, 45 wt % lactose, and 5 wt % sucrose. Sample 3 shows the solubility rate profile for granules formulated with a binder solution containing 50 wt % florfenicol, 47 wt % lactose, and 3 wt % Carbopol 940. Sample 4 shows the solubility rate profile for granules formulated with a binder solution containing 50 wt % florfenicol, 47 wt % lactose, and 3 wt % hydroxypropyl-cellulose. Sample 5 shows the solubility rate profile for pure florfenicol. The compositions of the samples is summarized below.

| | Composition (% w/w) | | | | | |
|---|---|---|---|---|---|---|
| | FFC | PVP30 | Lactose | Sucrose | Carbopol 940 | HPMC |
| Sample 1 | 50 | 3 | 47 | — | — | — |
| Sample 2 | 50 | — | 45 | 5 | — | — |
| Sample 3 | 50 | — | 47 | — | 3 | — |
| Sample 4 | 50 | — | 47 | — | — | 3 |
| Sample 5 | 100 | — | — | — | — | — |

FIG. 5 demonstrates that the composition of Sample 1 having the preferred water soluble binding agent PVP decreases the time that is necessary for florfenicol to dissolve in water, compared to the compositions of Samples 2, 3, 4 and 5. FIG. 5 also demonstrates that the compositions of Samples 2, 3, and 4 having a water soluble binding agent within the scope of the present invention also decrease the time that is necessary for florfenicol to dissolve in water, albeit that the time is longer than when the preferred water soluble binding agent PVP is employed.

Example 4

PVP30 was analyzed to determine its role in acting as a solubility enhancing agent for the active ingredient florfenicol in presence of Tween 80 as a surfactant.

Example 4 was prepared as soluble granules in the same manner described in Example 1 adding Tween 80 to the PVP30 binding solution. Solubility studies on this formulation have demonstrated that 100% of florfenicol was dissolved in within 15 minutes.

Although certain presently preferred embodiments of the invention have been described herein, it will be apparent to those skilled in the art to which the invention pertains that variations and modifications of the described embodiments may be made without departing from the spirit and scope of the invention.

Accordingly, it is intended that the invention be limited only to the extent required by the appended claims and the applicable rules of law.

We claim:

1. A method for antibiotic treatment of animals for pathogenic organisms susceptible to florfenicol, comprising:
   a) providing a soluble solid dosage form based florfenicol composition comprising:
      i) from about 20 to about 60 wt % of florfenicol or a pharmaceutically acceptable salt thereof,
      ii) from about 0.5 to about 5.0 wt % of a water soluble binding agent, and
      iii) from about 40 to about 80 wt % of a filler;
   b) dissolving the composition of step a) in water; and
   c) administering the water containing the florfenicol to the animals.

2. The method of claim 1, wherein the animal is swine, poultry or a bovid.

3. The method of claim 1, wherein the amount of the florfenicol or pharmaceutically acceptable salt thereof is from about 25 to about 50 wt % of the composition.

4. The method of claim 3, wherein the amount of the florfenicol or pharmaceutically acceptable salt thereof is from about 45 to about 50 wt % of the composition.

5. The method of claim 1, wherein the water soluble binding agent is polyvinylpyrrolidone, polyvinylpyrrolidone K30, sucrose, carboxy polymethylene, hydroxypropyl cellulose, starch, methylcellulose, sodium carboxymethylcellulose, polyacrilamide, polyvinyl alcohol, or a mixture thereof.

6. The method of claim 1, wherein the amount of the water soluble binding agent is from about 2.5 to about 3.5 wt % of the composition.

7. The method of claim 6, wherein the amount of the water soluble binding agent is from about 2.5 to about 3.0 wt % of the composition.

8. The method of claim 1, wherein the filler is lactose, sucrose, mannitol, sorbitol, calcium carbonate and/or a mixture thereof.

9. The method of claim 1, wherein the filler is from about 50 to about 75 wt % of the composition.

10. The method of claim 9, wherein the filler is from about 65 to about 70 wt % of the composition.

11. The method of claim 1, wherein the composition further comprises a surfactant.

12. The method of claim 11, wherein the surfactant is Tween 80, sodium lauryl sulfate, or a mixture thereof.

13. The method of claim 11, wherein the amount of the surfactant is from about 0 to about 10 wt % of the composition.

14. The method of claim 13, wherein the amount of the surfactant is from about 1 to about 5 wt % of the composition.

15. The method of claim 14, wherein the amount of the surfactant is from about 1 to about 3.5 wt % of the composition.

16. The method of claim 1, wherein the composition further comprises a wetting agent.

17. The method of claim 16, wherein the wetting agent is povidone, carbopol, sodium dodecyl sulfate, sodium lauryl sulfate, or a mixture thereof.

18. The method of claim 16, wherein the amount of the wetting agent is from about 0 to about 10 wt % of the composition.

19. The method of claim 18, wherein the amount of the wetting agent is from about 1 to about 5 wt % of the composition.

20. The method of claim 19, wherein the amount of the wetting agent is from about 1 to about 3.5 wt % of the composition.

21. The method of claim 1, wherein the composition further comprises a preservative.

22. The method of claim 1, wherein the concentration of the florfenicol or pharmaceutically acceptable salt thereof in the water is from about 0.01 mg/mL to about 0.2 mg/mL.

23. The method of claim 22, wherein the concentration of the florfenicol or pharmaceutically acceptable salt thereof in the water is from about 0.01 mg/mL±about 0.09 mg/mL.

24. The method of claim 5, wherein the water soluble binding agent is polyvinylpyrrolidone having a K value of from about 25 to about 35.

25. The method of claim 1, wherein the soluble solid dosage form-based florfenicol composition prior to admixture with water comprises:
   a) from about 25 to about 50 wt % of florfenicol;
   b) from about 2.5 to about 3.5 wt % of polyvinylpyrrolidone; and
   c) from about 50 to about 75 wt % of lactose,
   and the concentration of the florfenicol in the water after admixture is from about 0.01 mg/mL to about 0.2 mg/mL.

26. The method of claim 1, wherein the soluble solid dosage form-based florfenicol composition prior to admixture with water comprises:
   a) from about 45 to about 50 wt % of florfenicol;
   b) from about 2.5 to about 3.0 wt % of polyvinylpyrrolidone;
   c) from about 65 to about 70 wt % of lactose,
   and the concentration of the florfenicol in the water after admixture is from about 0.01 mg/mL±about 0.09 mg/mL.

27. A kit for antibiotic treatment of an animal for pathogenic organisms susceptible to florfenicol, comprising a soluble solid dosage form-based florfenicol composition comprising from about 20 to about 60 wt % of florfenicol or a pharmaceutically acceptable salt thereof, from about 0.5 to about 5.0 wt % of a water soluble binding agent, and from about 40 to about 80 wt % of a filler; instructions for dissolving the soluble solid dosage form-based florfenicol composition in water; and instructions for treating the animal with the water containing the florfenicol.

28. A method for the antibiotic treatment of an animal for pathogenic organisms susceptible to florfenicol, comprising dissolving a soluble solid dosage form-based florfenicol composition comprising from about 20 to about 60 wt % of florfenicol or a pharmaceutically acceptable salt thereof, from about 0.5 to about 5.0 wt % of a water soluble binding agent, and from about 40 to about 80 wt % of a filler in a sufficient amount of water to provide a florfenicol concentration of from about 0.01 mg/mL to about 0.09 mg/mL, and administering the water containing the florfenicol to the animal.

* * * * *